United States Patent [19]

Nishihara et al.

[11] Patent Number: 5,478,864

[45] Date of Patent: Dec. 26, 1995

[54] METHOD FOR DISINFECTION USING A 1,N-BIS($N^5$-TRIFLUOROMETHYL-PHENYL-$N^1$-BIGUANIDO)-ALKANE

[75] Inventors: Akira Nishihara; Akihiro Nakamura; Tsunetoshi Honda, all of Omiya; Michio Harada, Tokyo; Maki Takizawa, Hanno, all of Japan

[73] Assignees: Mitsubishi Materials Corp.; Yoshida Pharmaceutical Co., Ltd., both of Japan

[21] Appl. No.: 306,731

[22] Filed: Sep. 15, 1994

Related U.S. Application Data

[63] Continuation of Ser. No. 787,664, Dec. 9, 1992, abandoned.

[30] Foreign Application Priority Data

Dec. 12, 1991 [JP] Japan .................................. 3-351613
Dec. 12, 1991 [JP] Japan .................................. 3-351614

[51] Int. Cl.$^6$ ................................. A61K 31/155
[52] U.S. Cl. ................................. 514/635
[58] Field of Search ................................. 514/635

[56] References Cited

U.S. PATENT DOCUMENTS

2,684,924  7/1954  Rose et al. ........................... 514/635
4,067,962  1/1978  Juneja ................................... 514/635

FOREIGN PATENT DOCUMENTS

705838   2/1951  United Kingdom .
1549074  7/1976  United Kingdom .

OTHER PUBLICATIONS

Rose and Swain, Bisdiguanides having Antibacterial Activity, J.Chem. Soc., Jun. 19, 1956, pp. 4422–4425.

Warner & Lynch, Quantitative Structure–Activity Relationships for Biguanides . . . , J. Medicinal Chemistry, 1979, vol. 22, No. 4, pp. 359–366.

P. Gjiermo et al., Effect on Dental Plaque Formation and Some In Vitro Properties of 12 Bis–biguanides J.periodont.Res. 8; Suppl. 12: 81–88, 1973.

A. M. Slee et al., Studies on the Relative Binding Affinities of Chlorhexidine Analogs to Cation Exchange Surfaces, J.periodont.Res. 14: 213–219, 1979.

J. M. Tanzer et al., Structural Requirements of Guanide, Biguanide, and Bisbiguanide Agents for Antiplaque Activity, Antimicrobial Agents and Chemotherapy, vol. 12, No. 6, Dec. 1977, pp. 721–729.

V. D. Warner et al., 1,6–Bis ($N^5$–m–trifluoromethylphenyl–$N^1$biguanido)–hexane and Related Analogs of Chlorhexide as Inhibitors of Dental Plaque, J. Medicinal Che., 1973, vol. 16,No. 6, pp. 732–733.

*Primary Examiner*—Allen J. Robinson
*Assistant Examiner*—B. Bembenick
*Attorney, Agent, or Firm*—David G. Conlin; Peter F. Corless

[57] ABSTRACT

A novel disinfectant is disclosed. Said disinfectant is a compound 1,n-bis($N^5$-m-, or p-trifluoromethyl-phenyl-$N^1$-biguanido)-$C_3$-$C_{10}$-alkane. The m-trifluoro-$C_6$ derivative is a known compound. The compounds of the present invention exhibit germicidal effect against *Pseudomonas aeruginosa, Proteus vulgaris* and *Alcaligenes faecalis* at concentrations of ¼–⅛ of the effective concentration for chlorhexidine. Against other microorganisms, the compounds are effective at the same level as chlorhexidine.

12 Claims, No Drawings

METHOD FOR DISINFECTION USING A 1,N-BIS(N⁵-TRIFLUOROMETHYL-PHENYL-N¹-BIGUANIDO)-ALKANE

This is a continuation of application Ser. No. 07/987,664 filed on Dec. 9, 1992 (abandoned).

FIELD OF THE INVENTION

The present invention relates to a disinfectant. More particularly, the present invention relates to a group of bisbiguanide compounds and pharmaceutically acceptable salts thereof which are used as disinfectants.

BACKGROUND OF THE INVENTION

Chlorhexidine represented by the formula

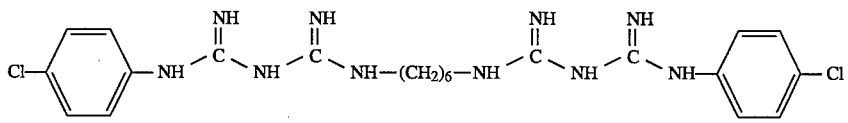

is a compound, which was developed in 1954 as a disinfectant, exhibits disinfecting effect on a wide range of general bacteria and is used in a very wide area because of its quick effect and low toxicity. Especially it is used as gluconate salt, which has high solubility in water, for disinfection of hands and fingers, operation localities and operation instruments in the medical field because of wide range germicidal activity.

However, chlorhexidine has a defect that it is less effective against some Gram-negative bacteria, especially *Pyocyaneus bacilli*. Further, recently *Pyocyaneus bacillus* strains and *Pseudomonas cepacia* strains, which are resistant to this drug, have been reported and now this is a problem in medical institutions. Chlorhexidine sometimes causes shock symptoms when it is administered to mucous membranes in a conventionally employed concentration and, therefore, administration thereof to mucous membranes other than conjunctivae is now prohibited.

Under the circumstances, a substitute for chlorhexidine, which retains the wide antibacterial spectrum of chlorhexidine and is provided with improved germicidal effect and medical applicability. That is, there is a demand for a chlorhexidine type disinfectant for medical use, which can be used in a low concentration so as to be safely applicable to mucous membranes, has improved germicidal activity especially against *Pyocyaneus bacilli* and is suitable as topical disinfectants for surgical operations.

V. D. Warner et al reported on dental plaque inhibiting (antiplaque) activities of bis-susbstituted 1,6-bis-biguanidohexane derivatives in Journal of Medical Chemistry, 1973, Vol. 16, No. 6, pages 732–733. It had been known that variation in the end substituents of 1,6-bis-biguanidine radically changes antibacterial activity of the compound. Warner et al reported that the bis-phenyl-substituted derivative exhibited no antiplaque activity, the bis-cyclohexyl-substituted and the bis-1-adamanthyl-substituted derivatives exhibited antiplaque activity at the same level as chlorhexidin or better and the bis(m-trifluoromethylphenyl) derivative exhibited superior antiplaque activity at lower concentrations.

It is more than twenty years since this report appeared and we know no report on further study on general germicidal activities of 1,6-bis-biguanidohexane derivatives.

We have taken up some α,ω-bis-biguanidoalkane derivatives and checked their antibacterial activities and we noted that 1,n-bis(N⁵-m- or p-trifluoromethylphenyl-N¹-biguanido)-$C_3$-$C_{10}$ alkanes exhibited excellent antibacterial activities.

SUMMARY OF THE INVENTION

This invention provides a disinfectant comprising 1,n-bis(N⁵-trifluoromethylphenyl-N¹-biguanido)-alkane represented by the formula

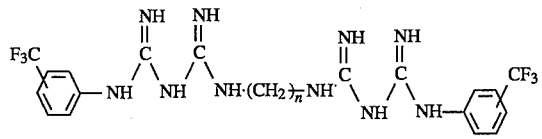

wherein n is an integer of 3–10 and the trifluoromethyl group is located at the m- or p-position, or a pharmaceutically acceptable salt thereof. One of these compounds, 1,6-bis(N⁵-m-trifluromethylphenyl-N'-biguanido)hexane is known and the others are novel compounds.

These compounds can be easily synthesized in accordance with the process described in J. Chem. Soc., 4422 (1956) for instance. That is, the compounds of which n is 6 can be synthesized by reacting 1,6-hexanediamine dihydrochloride with sodium dicyanamide to form 1,6-bis(N³-cyano-N¹-guanido)hexane and reacting the obtained 1,6-bis(N³-cyano-N¹-guanido)$^{hexane}$ with p- or m-trifluoromethylaniline hydrochloride. Each reaction is known per se and need not be described in detail.

The compounds of which n is other than 6 can be prepared in the same manner using corresponding α,ω-alkane diamines dihydrochloride.

The obtained compounds can be converted to their base by treating them with a base. Appropriate salts can be prepared by contacting the base with a corresponding acid. Of course it is possible to prepare a base first and to convert to a suitable salt.

Preferred acids are hydrochloric acid, acetic acid, gluconic acid, maleic acid, etc.

Specific Disclosure of the Invention

The invention will now be specifically described by way of working examples. However, these examples are merely illustrative and the invention is not limited thereto.

Example 1

Preparation of 1,6,bis($N^5$-p-trifluoromethylphenyl-$N^1$-biquanido)-hexane 1,6-Hexanediamine dihydrochloride (9.5 g, 50 mmol) and sodium dicyanamide (10.3 g, 100 mmol) were reacted in n-butanol under refluxing for 10 hours and 1,6-bis($N^3$-cyano-$N^1$-guanido)hexane (14.4 g (47.4 mmol)) was obtained.

The 1,6-bis($N^3$-cyano-$N^1$-guanido)hexane and 4-trifluoromethylaniline hydrochloride (24.9 g (126 mmol)) were reacted in 2-ethoxyethanol under refluxing for 15 hours. The deposited solid material was separated by filtration and combined with the solid material which was obtained by concentration of the filtrate and the combined solid material was recrystallized from a 50% acetic acid solution. Thus 21.8 g of hydrochloric acid salt of 1,6-bis($N^5$-p-trifluoromethylphenyl-$N^1$-biguanido)-hexane dihydrochloride was obtained as a white solid material.

The collected material was dissolved in 400 ml of a 1.5N hydrochloric acid solution and 100 ml of a 8N sodium hydroxide solution was added dropwise to the resulting solution. A solid substance deposited, which was collected, washed with water and recrystallized from ethanol. Thus 1,6-bis($N^5$-p-trifluoromethylphenyl-$N^1$-biguanido)-hexane was obtained. Identification data was as follows.

NMR Spectrum:

$^1$H-NMR (270 MHz, DMSO-$d_6$/TMS); δ1.32 ppm (brs, 4H), δ1.46 ppm (m, 4H), δ3.12 ppm (brs,4H), δ5.11 ppm (brs. 4H), δ6.97 ppm (d, 4H, J=8.0 Hz), 57.49 ppm (d, 4H, J=8.0 Hz), δ7.0–7.8 ppm (brs. 6H);

$^{13}$C-NMR (67.8 MHz, DMSO-$d_6$/TMS); δ26.07 ppm. δ29.12 ppm, δ40.17 ppm, δ120.04 ppm, (q. $J_{CF}$=31.2 Hz), δ122.96 ppm, δ124.96 ppm (q. $J_{CF}$=270.9 Hz), δ125.78 ppm (q. $J_{CF}$=3.2 Hz), δ154.68 ppm, δ158.07 ppm, δ158.18 ppm;

$^{19}$F-NMR(254 MHz, DMSO-$d_6$/TMS); δ59.22 ppm; IR Absorption spectrum (KBr tablet, cm$^{-1}$):

870, 1065, 1104. 1163, 1261, 1327, 1386, 1412, 1550, 1630, 1676, 3080; Mass Spectrum (20 eV, m/e):

161 (10.1%), 163 (21.4%), 204 (9.6%), 205 (9.6%), 188 (100%), 553 (0.3%), 571 (2.0%), 572 (2.1%)

Example 2

Preparation of digluconic acid salt

To 1,6-bis-($N^5$-p-trifluoromethylphenyl-$N^1$-biguanido-heane, 2 molar equivalent of gluconic acid (a 50% solution in distilled water) was added and the solution was suitably diluted. Thus 1,6-bis($N^5$-p-trifluoromethylphenyl-$N^1$-biguanido)-hexane digluconate aqueous solution was obtained.

Example 3

Evaluation of germicidal activity of the compound of Example 1

Germicidal activity of the compound prepared in Example 1 (Compound I) was evaluated by the minimum growth inhibition concentration method (based on the standard method stipulated by Japan Society of Chemotherapy) and the phenol coefficient method.

Evaluation of germicidal activity 1 (minimum growth inhibition concentration)

A portion of the digluconate salt of the compound of Example 1 was dissolved in water and the solution was heated to dryness on a water bath. The dried salt was dissolved in acetic acid (potentiometric titration grade) and the concentration thereof was determined by potentiometric titration using a perchloric acid solution. The gluconic acid salt solution, whose concentration was thus determined, was diluted to predetermined concentrations with sterilized water. Each 1 ml of the solution of each concentration was placed in a Petri dish, 9 ml of Mueller-Hinton agar (supplied by Difco) was added thereto and well mixed. Thus sensitivity test media were prepared. The concentrations of the compound were 200 μg/ml and $2^n$ times wherein (n=–8 to 2). Separately, microorganism strains indicated in Table 1 were subcultured in propagation media (using Mueller-Hinton broth supplied by Difco) at 37° C. for 24 hours. The microorganism concentration was adjusted to $10^6$/ml. The thus obtained cultures were respectively inoculated on a series of sensitivity measuring culture media using an inoculation rod. The minimum concentration at which growth of the microorganism was completely inhibited was determined. The results are shown in Table 1 together with the result on chlorhexidine as a control.

TABLE 1

| Microorganism | MIC (μg/ml) | |
|---|---|---|
| | CHXD | Ex. 1 |
| Alcaligenes faecalis IPO 13111 | 50 | 6.25 |
| Achromobacter xylosoxidans RIMD 0101001 | 25 | 50 |
| Flavobacterium meningosepticum RIMD 0614002 | 200 | 200 |
| Klebsiella pneumoniae IID 865 | 6.25 | 3.13 |
| Proteus vulgaris IID 874 | 200 | 25 |
| Pseudomonas aeruginosa IID 1042 | 100 | 12.5 |
| Pseudomonas aerugimosa (clinically collected) | 100 | 12.5 |
| Serratia marcescens IID 602 | 6.25 | 6.25 |
| Escherichia coli IID 861 | 1.56 | 3.13 |
| Escherichia coli IID 951 | 1.56 | 3.13 |
| Escherichia coli NIHJ JC-2 | 1.56 | 3.13 |
| Pseudomonas cepacia (collected Chiba Univ.) | 100 | 50 |
| Staphylococcus epidermis IID 866 | 1.56 | 1.56 |
| Staphylococcus aureus FDA 209-P | 0.78 | 1.56 |
| Staphylococcus aureus (clin'ly col'ted MRSA) | 6.25 | 6.25 |
| Staphylococcus aureus (clin'ly col'ted MRSA) | 3.13 | 1.56 |

CHXD: chlorhexidine (digluconate)
Ex. 1: compound of Example 1 (digluconate)

As seen in Table 1, the compound of Example 1 of the present invention exhibits germicidal effect against Pseudomonas aeruginosa, Proteus vulgaris and Alcaligenes faecalis at concentrations of ¼–⅛ of the effective concentration for chlorhexidine. Against other microorganisms, the compound is effective at the same level as chlorhexidine.

Evaluation of germicidal activity 2 (test for immediate effect)

Immediate effect of this compound was evaluated in accordance with the phenol coefficient method described in "Directions for Hygienic Tests" compiled by the Ministry of Health and Welfare of Japan. The method is as follows.

(1) Culture medium

Each 10 ml of the bouillon described below was taken into test tubes and they were sterilized with high pressure steam at 120° C. for 20 minutes.

Bouillon medium for testing disinfectants

| | |
|---|---|
| Peptone (product of Nippon Seiyaku) | 10 g |
| Meat extract (product of Kyokuto Seiyaku) | 5 g |
| NaCl (product of Kokusan Kagaku, special grade) | 5 g |
| Purified water | 1000 ml |
| pH 6.8 | |

(2) Test method

Diluted solutions of a series of concentrations of the sample compound were prepared for each of microorganisms listed in Table 2. Each 10 ml of the solutions was put into an appraisal test tube and the test tubes were placed in a thermostat bath kept at 20° C. Each microorganism was subcultured in the above described bouillon medium for testing disinfectants for three generations (37° C. for 48 hours). Each 1 ml of each culture was placed in each of the above-described series of appraisal test tubes and well mixed. After 2.5, 5, 10 and 15 minutes, 0.1 ml of the content of each appraisal test tube was taken and inoculated onto each portion of the bouillon medium for testing disinfectants. The portions were incubated at 37° C. for 48 hours and were observed for growth of the microorganisms. Each test was carried out three times. Immediate effect of disinfectants was compared by number of test runs in which microorganism growth was observed. The results are summarized in Table 2.

TABLE 2

| Microorganism | Conc. (%) | Sample | Contact Time (min) | | | |
|---|---|---|---|---|---|---|
| | | | 2.5 | 5.0 | 10.0 | 15.0 |
| *Escherichia coli* IID 861 | 0.001 | Ex. 1 | 3 | 3 | 2 | 1 |
| | | CHXD | 3 | 3 | 3 | 3 |
| *Pseudomonas aeruginosa* IID 1042 | 0.03 | Ex. 1 | 0 | 0 | 0 | 0 |
| | | CHXD | 2 | 1 | 0 | 0 |
| *Staphylococcus aureus* FDA 209-P | 0.0005 | Ex. 1 | 0 | 0 | 0 | 0 |
| | | CHXD | 3 | 1 | 0 | 0 |

Ex. 1: compound of Example 1 (digluconate)
CHXD: chlorohexidine (digluconate)

Example 4

Compounds of formula I, wherein the trifluoromethyl group is located at the p-position and n is 2, 3, 5, 8 and 11, were prepared starting from ethylene diamine dichloride, 1,3-propane diamine dichloride, 1,5-pentane diamine dichloride, 1,8-octane diamine dichloride or 1,11-undecane diamine dichloride, sodium dicyanamide and 4-trifluoromethyl aniline hydrochloride in accordance with the procedures as described above and minimum growth inhibition concentration (MIC) was determined in the same manner as above. The results are shown in Table 3.

TABLE 3

| Micro-organism | MIC (μg/ml) | | | | | |
|---|---|---|---|---|---|---|
| | *n = 2 | n = 3 | n = 5 | n = 6 | n = 8 | n = 11 |
| *Pseudomonas aeruginosa* IID 1042 | 200 | 50.0 | 12.5 | 12.5 | 25.0 | 400 |
| *Serratia marcescens* IID 602 | 50 | 6.25 | 6.25 | 6.25 | 6.25 | 100 |
| *Escherichia coli* IID 951 | 12.5 | 1.56 | 3.13 | 3.13 | 1.56 | 50 |
| *Staphylococcus aureus* FDA 209-P | 25.0 | 0.78 | 0.78 | 1.56 | 1.56 | 12.5 |

*Compounds of formula I, wherein the trifluoromethyl group is located at the p-position and n is 2, 3, 5, 6, 8 and 11

Example 5

Preparation of 1,6-bis(N$^5$-m-trifluoromethylphenyl-N$^1$-biguanido)-hexane

The procedures of Example 1 were repeated using 3-trifluoromethylaniline hydrochloride instead of 4-trifluoromethylaniline hydrochloride and 1,6-bis(N$^5$-m-trifluoromethylphenyl-N$^1$-biguanido)-hexane hydrochloride was obtained. Identification data was as follows.

NMR Spectrum:

$^1$H-NMR (270 MHz, DMSO-d$_6$/TMS); δ1.30 ppm (brs, 4H), δ1.47 ppm (m, 4H), δ3.12 ppm (d, 4H, J=6.8 Hz), δ6.8–8.3 ppm (m.18 H);

$^{13}$C-NMR (67.8 MHz, DMSO-d$_6$/TMS); δ25.90 ppm. δ28.62 ppm, δ40.90 ppm, δ116.81 ppm, δ118.17 ppm, δ124.15 ppm (q. J$_{CF}$=272.2 Hz), δ124.38 ppm. δ129.34 ppm (q,J=31.1 Hz), δ129.68 ppm, δ142.90 ppm, δ155.26 ppm; δ159.58 ppm;

$^{19}$F-NMR(254 MHz, DMSO-d$_6$/TMS); δ60.76 ppm; IR Spectrum (KBr tablet, cm$^{-1}$):

700, 798, 8 98. 1120, 1170, 1335, 1457, 1550, 1650, 3190, 3310; Mass Spectrum (20 eV, m/e):

161 (37.7%), 161 (37.7%), 163 (83.4%), 188 (100%), 204 (31.0%), 2.5 (30%), 415 (51.7%), 571(1.1%), 572 (1.0%)

Example 6

Preparation of digluconic acid salt

To 1,6-bis-(N$^5$-m-trifluoromethylphenyl-N$^1$-biguanido)-hexane, 2 molar equivalent of a 50% aqueous solution of gluconic acid (in distilled water) was added and the solution was suitably diluted. Thus 1,6-bis(N$^5$-m-trifluoromethylphenyl-N$^1$-biguanido)-hexane digluconate aqueous solution was obtained.

Example 7

Evaluation of Disinfecting Effect

Disinfecting effect of the above-prepared compounds was tested by measurement of minimum growth inhibition concentration and by the test for immediate effect in the same manner as in Example 3. The results were as follows.

Evaluation of germicidal activity 1(minimum growth inhibition concentration)

TABLE 4

| Microorganisms | MIC (μg/ml) | |
|---|---|---|
| | CHXD | Ex. 5 |
| *Alcaligenes faecalis* IPO 13111 | 50 | 6.25 |
| *Achromobacter xylosoxidans* RIMD 0101001 | 25 | 25 |
| *Flavobacterium meningosepticum* RIMD 0614002 | 200 | 200 |
| *Klebsiella pneumoniae* IID 865 | 6.25 | 1.56 |
| *Proteus vulgaris* IID 874 | 200 | 12.5 |
| *Pseudomonas aeruginosa* IID 1042 | 100 | 25 |
| *Pseudomonas aerugimosa* (clinically collected) | 100 | 25 |
| *Serratia marcescens* IID 602 | 6.25 | 6.25 |
| *Escherichia coli* IID 861 | 1.56 | 1.56 |
| *Escherichia coli* IID 951 | 1.56 | 1.56 |
| *Escherichia coli* NIHJ JC-2 | 1.56 | 1.56 |
| *Pseudomonas cepacia* (collected Chiba Univ.) | 100 | 50 |
| *Staphylococcus epidermis* IID 866 | 1.56 | 1.56 |
| *Staphylococcus aureus* FDA 209-P | 0.78 | 0.78 |
| *Staphylococcus aureus* (clin'ly col'ted MRSA) | 6.25 | 3.13 |
| *Staphylococcus aureus* (clin'ly col'ted MRSA) | 3.13 | 1.56 |

CHXD: chlorhexidine (digluconate)
Ex. 5: compound of Example 5 (digluconate)

For some microorganism strains, the results are apparently the same as the results with respect to the compound of Example 1. In the case of a dilution method, this will happen when the effects of two compounds are of the same level.

Effect of Germicidal Activity 2 (test for immediate effect

The results of the immediate effect test are indicated in Table 5.

TABLE 5

| Microorganism | Conc. (%) | Sample | Contact Time (min) | | | |
|---|---|---|---|---|---|---|
| | | | 2.5 | 5.0 | 10.0 | 15.0 |
| *Escherichia coli* IID 861 | 0.001 | Ex. 1 | 2 | 1 | 0 | 0 |
| | | CHXD | 3 | 3 | 3 | 3 |
| *Pseudomonas aeruginosa* IID 1042 | 0.03 | Ex. 1 | 0 | 0 | 0 | 0 |
| | | CHXD | 2 | 1 | 0 | 0 |
| *Staphylococcus aureus* FDA 209-P | 0.0005 | Ex. 1 | 0 | 0 | 0 | 0 |
| | | CHXD | 3 | 1 | 0 | 0 |

Example 8

Compounds of formula I, wherein the trifluoromethyl group is located at the m-position and n is 2, 3, 5 and 8, 11 were prepared starting from ethylene diamine dihydrochloride, 1,3-propane diamine dihydrochloride, 1,5-pentane diamine dihydrochloride, 1,8-octane diamine dihydrochloride or 1,11-undecane diamine dihydrochloride, sodium dicyanamide and 3-trifluoromethylaniline hydrochloride in accordance with the procedures of Example 4 and germicidal activity thereof were determined in the same manner. The results are shown in Table 6.

TABLE 6

| Micro-organism | MIC (µg/ml) | | | | | |
|---|---|---|---|---|---|---|
| | *n = 2 | n = 3 | n = 5 | n = 6 | n = 8 | n = 11 |
| *Pseudomonas aeruginosa* IID 1042 | 200 | 50.0 | 12.5 | 25.0 | 25.0 | 400 |
| *Serratia marcescens* IID 602 | 50 | 12.5 | 6.25 | 6.25 | 6.25 | 100 |
| *Escherichia coli* IID 951 | 12.5 | 3.13 | 3.13 | 1.56 | 1.56 | 25 |
| *Staphylococcus aureus* FDA 209-P | 12.5 | 3.13 | 0.78 | 0.78 | 1.56 | 12.5 |

*Compounds of formula I, wherein the trifluoromethyl group is located at the m-position and n is 2, 3, 5, 6, 8 and 11

What we claim is:

1. A method for disinfecting hands and fingers, operation localities, and operation instruments from one or more bacteria species selected from the group consisting of *Pseudomonas aeruginos*, methicillin-resistant *Staphylococcus aureus*, *Alcaligenes faecalis*, *Klebsiella pneumoniae*, *Proteus vulgaris* and *Pseudomonas cepacia*, said method comprising using a solution of (i) a 1,n-bis(N$^5$-trifluoromethylphenyl-N$^1$-biguanido)-alkane represented by the formula:

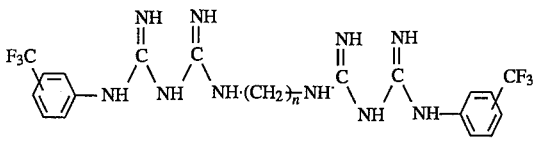

wherein n is an integer of 5 or 6 and the trifluoromethyl group is located at the m-position or p-position or (ii) a pharmaceutically acceptable salt thereof.

2. The method of claim 1 wherein said hands and fingers, operation localities, and operation instruments are disinfected from one or more bacteria species selected from the group consisting of *Pseudomonas aeruginosa* and methicillin-resistant *Staphylococcus aureus*.

3. The method of claim 1 wherein said hands and fingers, operation localities, and operation instruments are disinfected from *Pseudomonas aeruginosa*.

4. The method of claim 1 wherein said hands and fingers, operation localities, and operation instruments are disinfected from methicillin-resistant *Staphylococcus aureus*.

5. The method of claim 1 wherein said hands and fingers, operation localities, and operation instruments are disinfected from *Alcaligenes faecalis*.

6. The method of claim 1 wherein said hands and fingers, operation localities, and operation instruments are disinfected from *Klebsiella pneumoniae*.

7. The method of claim 1 wherein said hands and fingers, operation localities, and operation instruments are disinfected from *Proteus vulgaris*.

8. The method of claim 1 wherein said hands and fingers, operation localities, and operation instruments are disinfected from *Pseudomonas cepacia*.

9. The method as claimed in claim 1, wherein the trifluoromethyl group is located at the p-position.

10. The method as claimed in claim 9, wherein n is 6.

11. The method as claimed in claim 4, wherein the trifluoromethyl group is located at the m-position.

12. The method as claimed in claim 11, wherein n is 6.

* * * * *